US00PP19759P2

(12) United States Plant Patent
Easey

(10) Patent No.: US PP19,759 P2
(45) Date of Patent: Feb. 24, 2009

(54) LIVE OAK TREE NAMED 'FBQV1'

(50) Latin Name: *Quercus virginiana*
Varietal Denomination: FBQV1

(75) Inventor: Norman C. Easey, Sarasota, FL (US)

(73) Assignee: Fish Branch Tree Farm, Inc., Zolfo Springs, FL (US)

( * ) Notice: Subject to any disclaimer, the term of this patent is extended or adjusted under 35 U.S.C. 154(b) by 74 days.

(21) Appl. No.: 11/648,342

(22) Filed: Dec. 28, 2006

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

| | | | |
|---|---|---|---|
| PP11,097 | P | 10/1999 | Sallin |
| PP11,219 | P | 2/2000 | Strickland |
| PP12,015 | P2 | 7/2001 | Reeves |

*Primary Examiner*—Kent L Bell
(74) *Attorney, Agent, or Firm*—Klarquist Sparkman, LLP

(57) ABSTRACT

A distinct variety of live oak (*Quercus virginiana*) named 'FBQV1' which is distinctive in having a dense, broadly pyramidal shaped, upright canopy; a dominant central leader; well placed scaffold branches and numerous small lateral spur branches, generally without included bark in the branch unions; mature dark foliage with leaves typically being about one and one-quarter inches to two and one-half inches long and about three-eighths to about one-half inch wide; and an evergreen habit. The canopy is very dense with interior and exterior foliage provided by abundant interior spur branches.

3 Drawing Sheets

Latin name of genus and species: *Quercus virginiana.*
Variety denomination: 'FBQV1'.

BACKGROUND OF THE INVENTION

The present invention relates to a new and distinct variety of *Ouercus virginiana* (Live oak) referred to by the varietal name 'FBQV1'.

The original 'FBQV1' tree was initially discovered as a seedling growing in a cultivated area of the Fish Branch Tree Farm, in Zolfo Springs, Fla., among a group of cultivated Live Oak seedlings. These seedlings had been acquired from a grower of "liners" when they were about twelve to fourteen inches tall. These seedlings had been grown from seed. The parent trees of these seedlings and therefore of the original tree of this new variety are both unknown to the inventor.

'FBQV1' was observed to have a broad upright habit and a dominant leader, dark-green foliage color similar to common seedling Live Oak trees observed by the inventor, dense foliage arrangement, and true evergreen habit. Compared to common seedling Live Oak trees observed by the inventor, this initially discovered tree had a rapid growth rate, generally lacked included bark, had small diameter lateral spurs, had leaves which were typically about one and one-quarter inch to two and one-half inches long by about three-eighths inch to one-half inch wide and which were consistently relatively dark green when mature, and exhibited a dense, broadly upright pyramidal canopy. The new variety has a broad upright habit of growth and a dominant leader. These characteristics of my new variety have been observed to be fixed and reproduce true to type in progeny from asexually propagated cuttings from the initially discovered tree. Asexual propagation was performed at a nursery in Zolfo Springs, Fla.

BRIEF SUMMARY OF THE INVENTION

The 'FBQV1' variety has not been observed under all growing conditions and thus variations may occur as a result of different growing conditions. The observations are of the original tree and six year old asexually propagated trees of my new variety growing in Zolfo Springs, Fla. and in Sarasota, Fla.

'FBQV1' has an unusually broadly pyramidal canopy with truly evergreen foliage compared to the species in general. It also has a broader width to height ratio as compared to its nearest variety 'SDLN' (U.S. Plant Pat. No. 12,015). At nine years of age, the original tree of my variety had a width to height ratio of about 0.68 (height to width ratio 1.47). A group of ten typical six year old asexually propagated trees of my new variety growing in Zolfo Springs, Fla., had an average width to height ratio of about 0.64, (11.7 feet wide to 18.2 feet tall). The height to width ratio in this example was 1.56.

The leaves of 'FBQV1' variety are a slightly darker green than those of common seedling Live Oak trees which I have observed growing in the same general area and mature leaves have been observed to not change color significantly with the seasons.

Unlike the common seedling Live Oak trees I have observed, the 'FBQV1' variety has superior apical dominance with a single dominant leader. Common seedling Live Oak trees observed by the inventor have a spreading growth habit where the width of the canopy substantially exceeds the height of the tree. In 'FBQV1', however, the tree forms a very dense, distinctive and desirable broadly upright, pyramidal growth habit. There are also an unusual number of temporary secondary spur branches held along main branches and trunk. Secondary spur branches are branches that typically grow to about twelve inches to eighteen inches and then stop growing. These secondary spur branches eventually die and are shed.

Branches arise at wide angles (most lateral branches have branch crotch angles greater than sixty degrees), minimizing formation of included bark. Well spaced scaffold lateral branches make this plant easier to prune into a strong structure with a central leader. The canopy is very dense with interior and exterior foliage provided by abundant interior spur branches. This new variety is easy to root. For example, in a specific observation, there was a greater than 50 percent take rate for cuttings directly from the initially discovered tree and, in another observation, approximately 70 percent of the cuttings from 2 to 3 year old second-generation trees rooted.

This extremely high asexual reproduction rate was obtained by preparing the cutting wood in the following manner a.) Six to eight inch-long stem and terminal cuttings, each with eight to ten leaves, were collected in the first week of May from the initially discovered tree.

b.) Cuttings were quick dipped in a solution of 10,000 ppm of KIBA (Potassium salt Indole-3-butyric acid) and 5000 ppm of KNAA (Potassium salt napthalane-acetic acid).

c.) Cuttings were placed in two and one quarter by four inch air root pruning containers, filled with appropriate media.

d.) Plants were placed in a mist house and misted with two seconds mist spray every four to five minutes.

e.) Plants remained in the mist house for ten to twelve weeks. Seventy five percent of these cuttings rooted.

The 'FBQV1' variety has a slightly faster growth rate compared to common seedling Live Oak trees observed by the inventor and growing in the same area. The trunk diameter, taken at twelve inches above ground of the initially discovered tree of the new variety, aged five years and growing in Zolfo Springs, Fla., measured approximately 4 inches caliper, while common seedling Live Oak trees of the same age and observed by the inventor growing in the same area had a three to four inch caliper, measured at twelve inches from the ground. The initially discovered tree and asexually propagated progeny have a broadly upright habit and a dominant leader.

BRIEF DESCRIPTION OF THE DRAWINGS

The accompanying photographs depict the color of the tree and foliage of my new variety as nearly as is reasonably possible to make the same in a color illustration of this character.

DETAILED BOTANICAL DESCRIPTION

Figure 1:
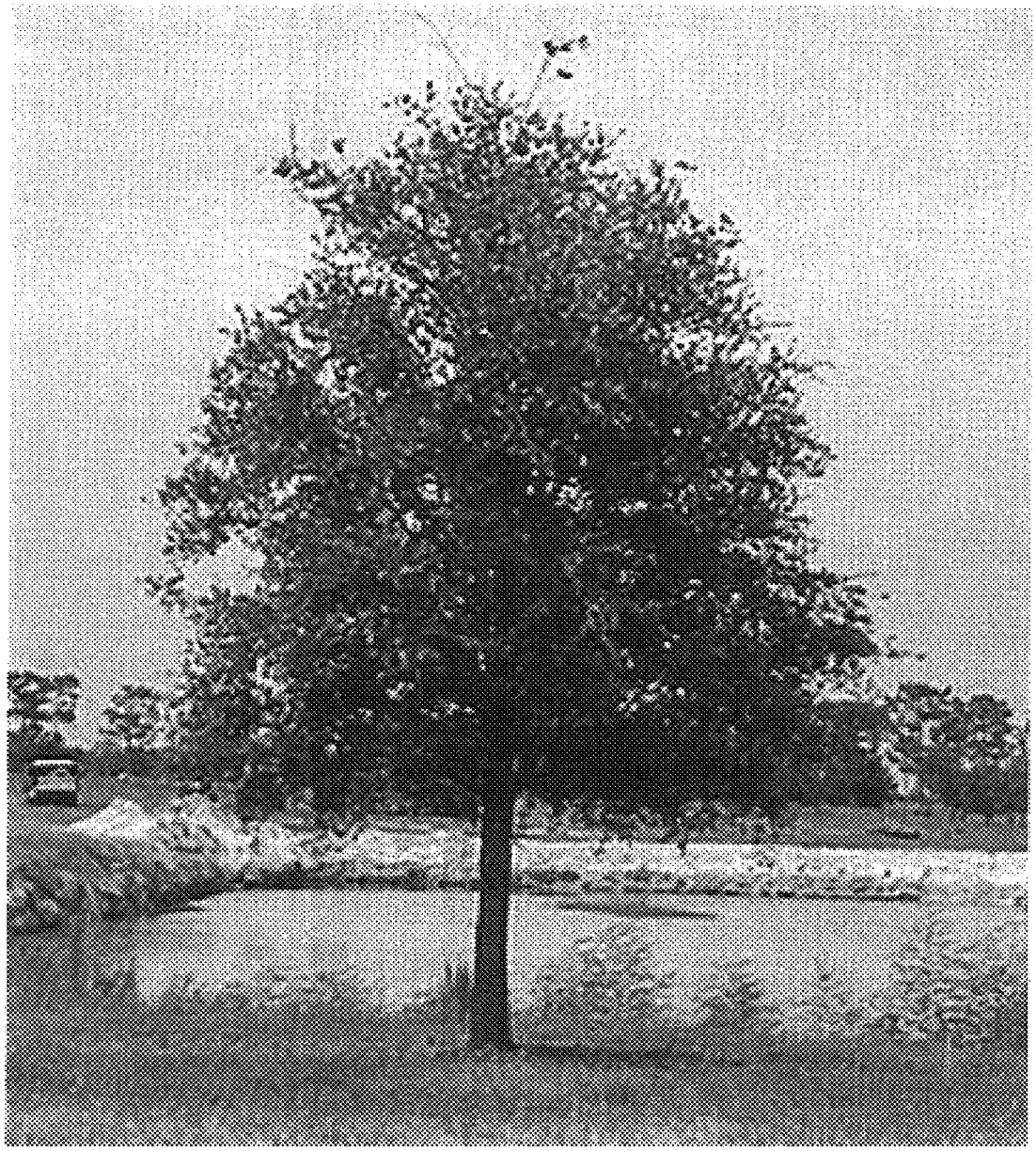
FIG. 1 depicts the initially discovered tree of my new variety showing the broadly pyramidal canopy shape, upright habit, and a single, dominant leader. When this picture was taken, the initially discovered tree was ten years of age, was twenty two feet tall by fifteen feet wide with a nine and one-quarter inch caliper, measured at twelve inches from the ground, and was growing in Zolfo Springs, Fla.
Figure 2:
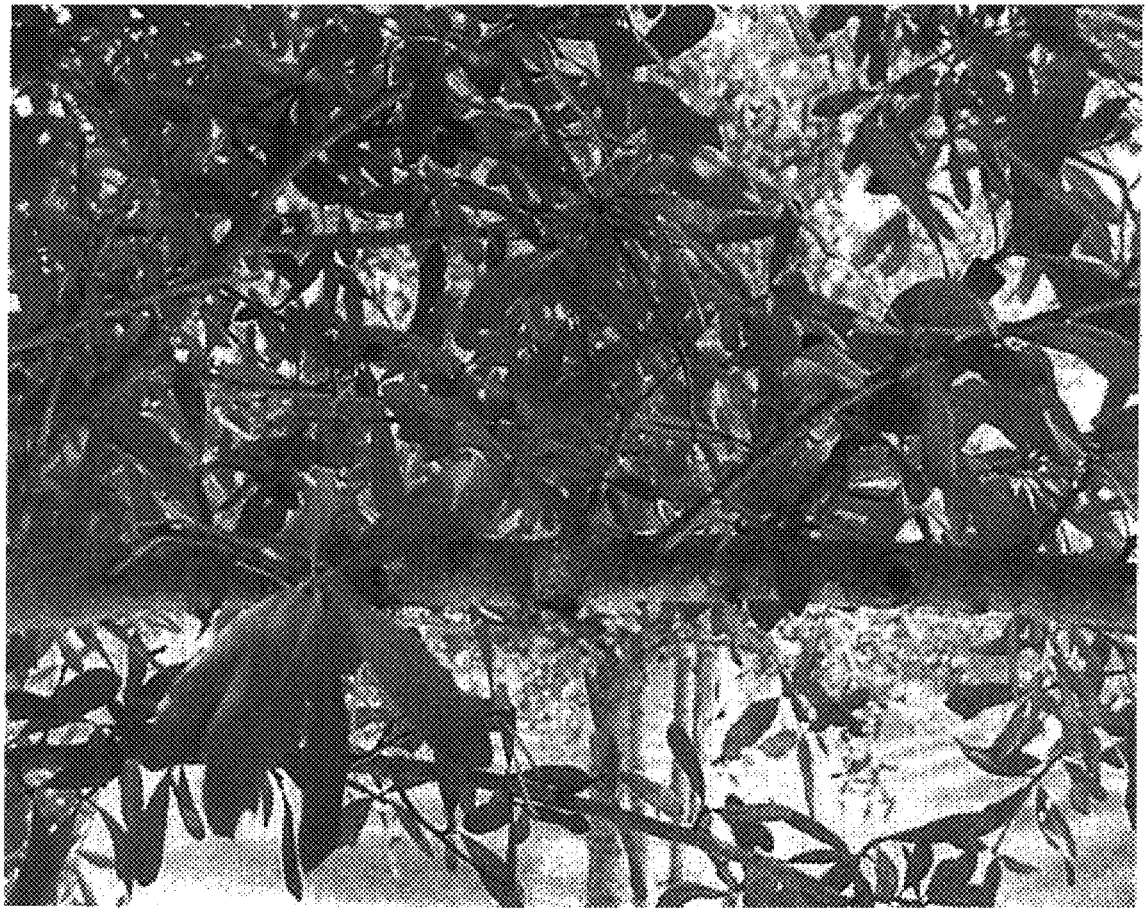
FIG. 2 shows the dense arrangement of spur branches along a main branch.
Figure 3:
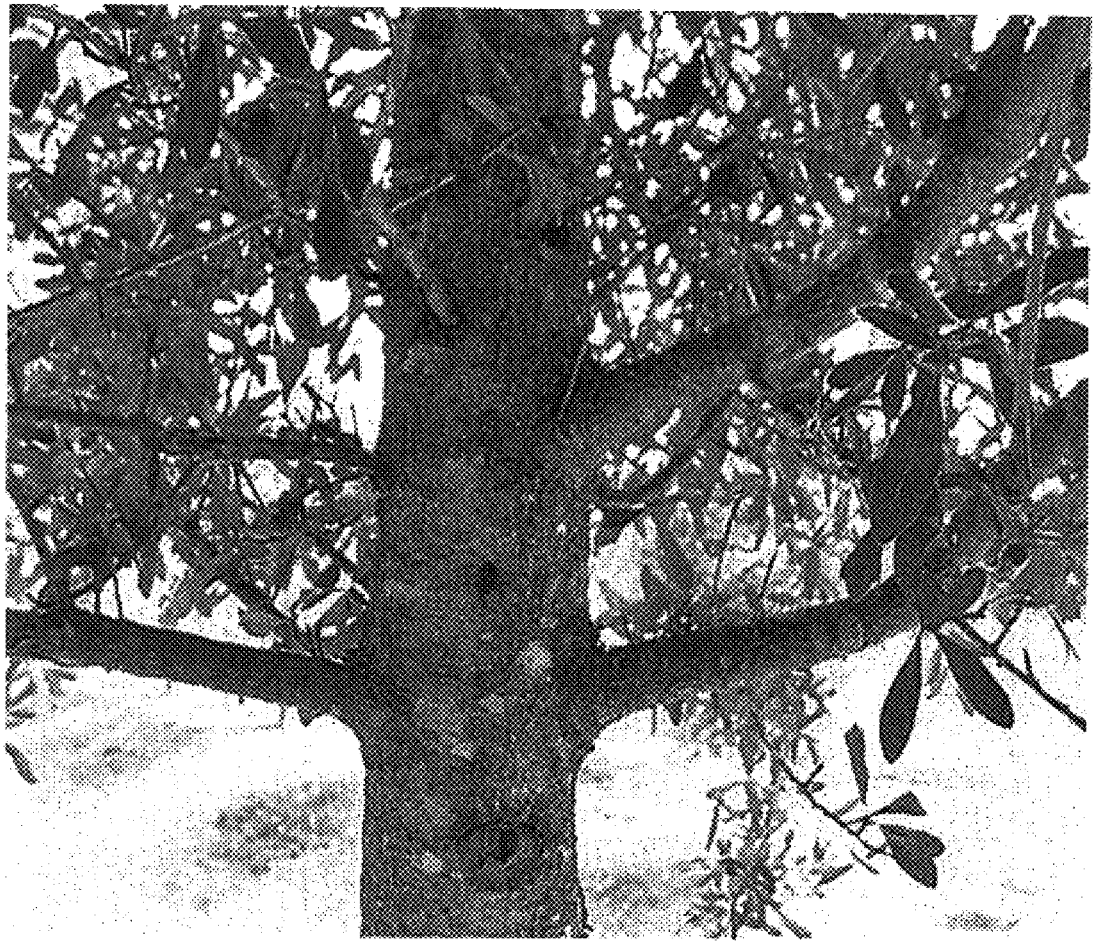
FIG. 3 shows branches arising at a wide angle and lack of included bark.

The following is a description of my new variety of Live Oak tree. Except as otherwise indicated, the observations are of the original tree at age ten years from acorn. Color terminology in accordance with The Royal Horticultural Society Colour Chart (R.H.S.), except where the context indicates a term having it ordinary dictionary meaning. All color measurements were taken under bright shade conditions.

All Live Oak trees of my new variety, insofar as have been observed, have been identical in all characteristics described below. Other than as set below, as of this time no other characteristics have been observed which are different from seedling Live Oak trees which have been observed by the inventor.

Parentage: Seedling of unknown parentage.

Locality where grown and observed: Zolfo Springs, Fla. and Sarasota, Fla..

Leaves:

*Shape and arrangement.*—Simple leaves; elliptic to oblong or obovate; alternate arrangement; Base — typically acute, sometimes observed as cuneate to rounded; Apex — typically acute, sometimes observed as obtuse; prominent mid-rib underneath with typically ten to eleven main veins from the mid-rib, vein color typically yellow-green (RHS yellow-green 150B); Margin — entire with occasional acute lobes or teeth; slightly tomentose underneath; stiff; slight downward recurved margin.

*Size.*—Length — Variable, typically one and one-quarter inches to two and one-half inches, most average one and three-fourths inches; Width — variable, typically three-eighths inch to one-half inch, most averaging one-half inch.

*Color.*—Evergreen tree with leaves that shed as buds emerge. Emerging leaves — typical upper surface, maroon to red-purple (RHS red-purple 178B); typical lower surface, yellow-green (RHS yellow-green 148C); Young summer leaves — typical upper surface, dark green (RHS dark green 137A); typical lower surface, dark yellow-green (RHS yellow-green 146B); Mature summer leaves — typical upper surface, dark yellow-green (RHS yellow-green 147A); typical lower surface, dark yellow-green (RHS yellow-green 146B).

*Petiole.*—Length — variable, typically one-sixteenth inch to one-eighth inch long; Width — variable, typically one-thirty-second inch to one-sixteenth inch wide;

*Color.*—variable, upper surface color observed as greyed-red (RHS 179B); lower surface color observed as greyed-red with yellow-green (RHS greyed-red 178C with RHS yellow-green 151B).

Buds:

*Shape.*—Variable, subglobose to globose, typically globose;

*Size.*—Length — typically one thirty-second inch to one-sixteenth inch; Width — variable, typically one thirty-second inch to one-sixteenth inch;

*Color.*—Greyed-orange (RHS greyed-orange 175B).

Flowers and reproductive organs:

*Location.*—Typical of species — male in catkins, female in axils of leaves;

*Initial flowering season.*—March in Central Florida.

Fruit: Acorns: (Observed in both original tree and progeny)

*Number in clusters.*—The initially discovered tree has produced acorns typical of the species; typically one acorn per cluster, sometimes observed as two acorns per cluster;

*Maturation.*—Acorns mature in one growing season and typically fall from the tree in October through November in Central Florida;

*Shape.*—Acorns are oval to ovate and short pointed at the apex;; no circular scar observed at base.

*Size.*—Typical, representative observed acorns were seven-eighths inch to one inch in length and three-eighths inch to seven-sixteenths inch wide;

*Color.*—Typical upper acorn coloration, under the acorn cap, colored greyed-yellow (RGS greyed-yellow 160C) and typical lower acorn coloration is brown (RHS brown 200B);

Acorn Caps:

*Size.*—Typical acorn cap is seven-sixteenths inch to nine-sixteenths inch in width and seven-sixteenths inch in length; Typical peduncle is one half inch to seven-sixteenths inch long and one sixteenth inch to three thirty seconds inch in diameter;

*Color.*—Acorn cap is typically colored greyed-green (RHS greyed-green 197C), and scaly with a finely serrated edge; typical peduncle is colored greyed-brown (greyed-brown 199C). No spots have been observed on the cap.

Stem: Color — Emerging young stems maroon (RHS red-purple 178A) turning light gray (RHS grayed-green 197B). Mature stems greyed-green (RHS greyed-green 198A);

*Description.*—Glabrous, no inclusions;

Branch attachment: Branches of a six year old tree are typically five and one half to six and one half feet in length and three quarter inch to one inch in diameter, measured at a distance of six inches from the main trunk; branches arise randomly at a typical branch angle of sixty to ninety degrees from the main trunk, other than spur branches, branches on this tree were typically spaced four to fifteen inches apart.

Trunk: Color — Light grey (RHS greyed-green 198A) becoming slightly fissured and darker (RHS 198B) on older sections. Smooth texture.

Growth habit: Broadly upright, pyramidal.

Vigor: The initially discovered tree and young rooted plants have been observed to grow about three feet in height each year, and the trunk diameter has been observed to increase in caliper one and one quarter inches each year after the first year.

Propagation: Holds to distinguishing characteristics through succeeding propagation by rooted cuttings.

Disease and pest resistance: Gall insects sometimes found on small branches; no other diseases or insects observed on trees to date.

I claim:

1. A new and distinct variety of Live Oak (*Ouercus virginiana*) tree named 'FBQV22', substantially as herein shown and described.

* * * * *